United States Patent [19]

Lieberman et al.

[11] Patent Number: 5,473,952
[45] Date of Patent: *Dec. 12, 1995

[54] BENTHIC FLUX SAMPLING DEVICE

[75] Inventors: Stephen H. Lieberman; David B. Chadwick, both of San Diego; David R. Bower, Ridgecrest, all of Calif.

[73] Assignee: The United States of America as represented by the Secretary of the Navy, Washington, D.C.

[*] Notice: The term of this patent shall not extend beyond the expiration date of Pat. No. 5,395,568.

[21] Appl. No.: 217,474

[22] Filed: Mar. 22, 1994

[51] Int. Cl.⁶ ..................................................... G01N 1/00
[52] U.S. Cl. ........................ 73/864.31; 73/863.01
[58] Field of Search ............................ 73/863.31, 863.34, 73/863.81, 863.82, 863.02, 864.31, 864.63, 864.65, 864.66, 864.67, 864.35, 863.01, 863.03

[56] References Cited

U.S. PATENT DOCUMENTS

| | | |
|---|---|---|
| 3,199,070 | 8/1965 | Baier, Jr. . |
| 3,845,303 | 10/1974 | Richards et al. . |
| 3,987,677 | 10/1976 | Alter . |
| 4,089,209 | 5/1978 | Grana et al. . |
| 4,166,392 | 9/1979 | Farnworth . |
| 4,336,709 | 6/1982 | Meek ................................ 73/864.67 |
| 4,454,773 | 6/1984 | Brunner et al. ..................... 73/863.31 |
| 4,454,774 | 6/1984 | Pridgen ............................. 73/864.51 |
| 4,762,009 | 8/1988 | Scrudto . |
| 5,062,309 | 11/1991 | Voll et al. . |
| 5,085,085 | 2/1992 | Anderson ........................... 73/863.02 |
| 5,167,802 | 12/1992 | Sandstrom et al. . |
| 5,172,332 | 12/1992 | Hungerford et al. . |
| 5,395,568 | 3/1995 | Chadwick ............................ 261/36.1 |

*Primary Examiner*—Richard Chilcot
*Assistant Examiner*—Max Noori
*Attorney, Agent, or Firm*—Harvey Fendelman; Thomas Glenn Keough

[57] ABSTRACT

A method for sampling toxin flux rates across a benthic boundary relies upon deploying an apparatus having a frame which houses a container having an open bottom for isolating a volume of fluid above a benthic fluid boundary. A sampling system periodically samples and stores samples of the isolated fluid and an oxygenation system maintains a constant dissolved oxygen level within the container. The device is then retrieved and the samples analyzed. In this way, the toxin flux rate across the fluid boundary may be determined.

35 Claims, 10 Drawing Sheets

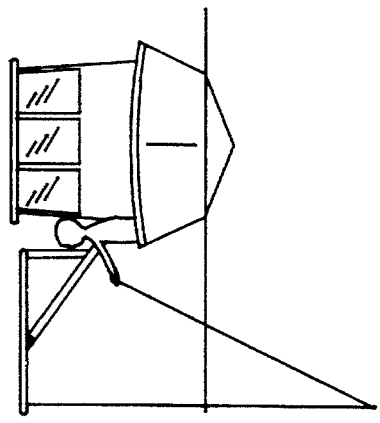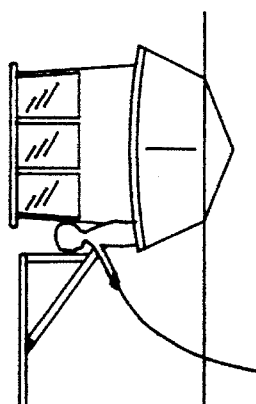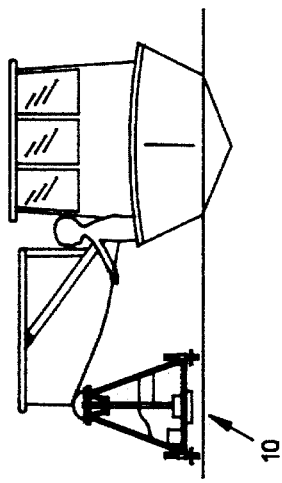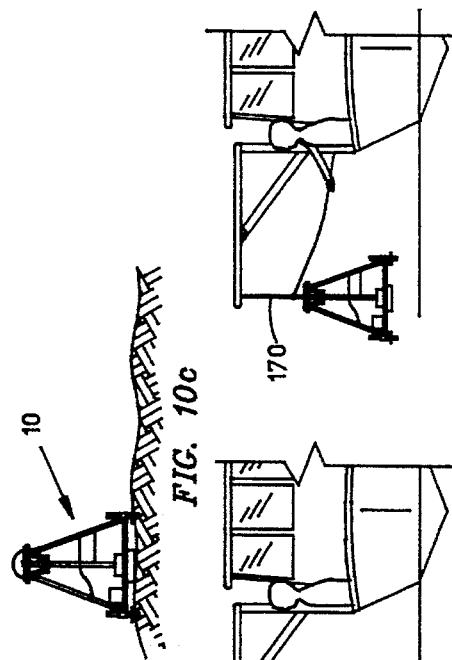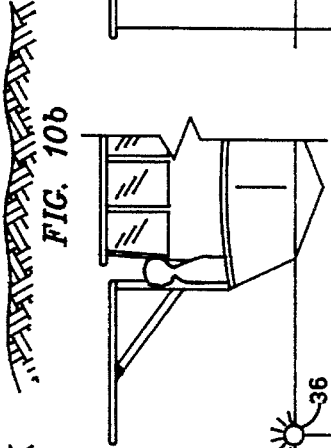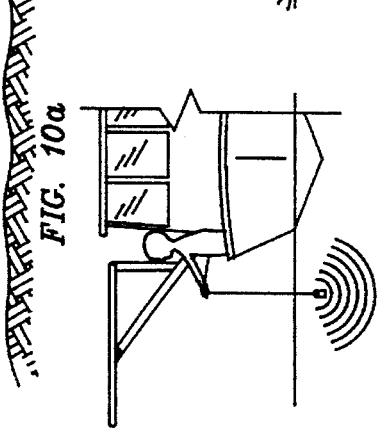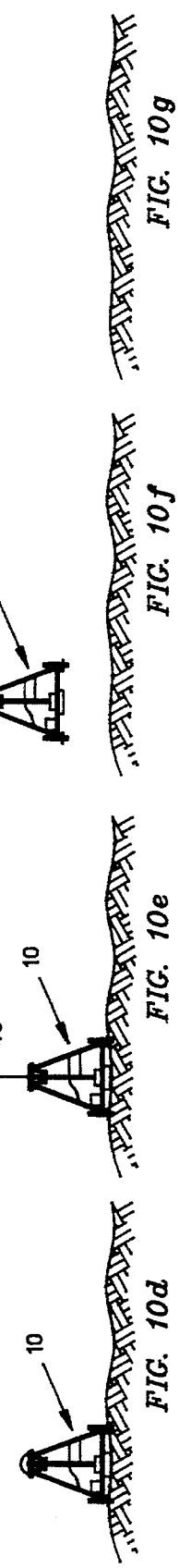

5,473,952

BENTHIC FLUX SAMPLING DEVICE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates generally to fluid sampling and more particularly to methods of sampling toxin flux rates across the sediment/water interface at the ocean floor.

Sediment in many bays, harbors and coastal waters 1s contaminated with metal and organic toxins. These toxins are known to cause extensive biological harm to aquatic environments. As a result of the threat of biological harm, remedies for contamination due to toxins are continually being devised.

In order to effectuate a satisfactory remedy however, the source of contamination must first be identified. The remedial urgency (i.e. biological risk) relative to other contaminated sites must also be determined. With toxin sources identified and biological risk assessed, remedial resources can be efficiently allocated to remedy contamination caused by toxins.

Historically, industrial discharge, chemical spills, improper waste disposal and urban runoff have been the largest known toxin sources. These sources are relatively easy to pin point. It is now known, however, that a significant portion of aquatic contamination comes via pore water and particulate bound contaminate exchange in benthic sediment (i.e. soluble toxins are suspended and leached from underwater sediment into the aquatic environment).

Sedimentary (benthic) contamination is particularly troublesome to remedy because, unlike contamination caused by chemical spills and industrial discharge, the source is often difficult to pinpoint. Benthic contamination also creates a high level of biological risk for benthic organisms whose survival depends on the condition of the underwater sediment. Additionally, as toxins in the underwater sediment migrate across the sediment/water interface and into the aquatic environment, all aquatic organisms are put at risk of contamination. Due to the scope and seriousness of problems associated with benthic contamination, a myriad of approaches have been developed to measure toxin levels in benthic sediments.

One common approach has been to remove and transport a sediment sample to a laboratory for chemical and biological testing. This approach requires numerous samples and is thus time consuming, expensive and inefficient. Inaccuracy is caused by sediment removal prior to testing. More specifically, removal of a sample disturbs the sediment so that natural conditions present at the site may not be well preserved in the laboratory. Localized variables such as underwater pressure, temperature, salinity, pH, oxygen and light intensity effect sediment samples. As toxin levels and bioavailability directly depend on these localized variables, toxin levels and toxicity in laboratory test samples do not always coincide with those detected under natural conditions.

Besides inaccuracy, another problem associated with previous method of sediment testing is that it is not capable of yielding changes in toxin concentrations. Since several samples taken at a single point are required to determine change in toxin concentrations and the act of removing sediment samples disturbs nearby sediment, tiny changes in toxicant levels can not be ascertained with any useful degree of certainty.

Toxin concentration by itself is not indicative of the level of biological risk. To precisely determine biological risk, the biological uptake and accumulation of toxicant by marine life must be determined. Unfortunately, direct measurement of these factors is extraordinarily difficult. Indirect measurements, however, may be made. This is accomplished by measuring the amount of soluble toxins which leach through pore water, cross the sediment water boundary and enter the aquatic environment. This is called the benthic flux rate.

The benthic flux rate is the most accurate known indicator of the rate at which toxins are entering an aquatic environment from the sediment. The benthic flux rate is also useful in pinpointing the source of contamination by determining whether toxins are leaching from the sediments into the water or vice versa. Together with traditional monitoring and assessment techniques, these benthic flux measurements are effective for determining the source of and biological risk associated with contamination of benthic sediments.

In view of the inefficiency, inaccuracy and imprecision of the other sediment sampling methods and in accordance with this inventive concept, a need has become apparent for an improved method of benthic flux sampling which includes isolating a volume of water on the ocean floor in a closed chamber, measuring variables such as temperature, salinity, pH and dissolved oxygen concentration and maintaining appropriate oxygen levels to insure precise and accurate toxin concentration determination by periodic sampling to ascertain the benthic flux rate.

SUMMARY OF THE INVENTION

In accordance with the present invention, a method for measuring toxin flux rates across a fluid boundary (e.g. across sediments at the ocean floor) is provided. The method, generally stated, includes deploying a benthic flux sampling device on the ocean floor and thereby isolating a sample volume of water and maintaining oxygen levels within the sample. Conditions such as temperature, conductivity, and pH and dissolved oxygen content within the sample are monitored. Periodic samples of water are taken and stored so that the samples may be analyzed later. The benthic flux sampling device is then retrieved. From the samples and data obtained, the rate at which toxins flow from the benthic sediments into the water is determinable.

BRIEF DESCRIPTION OF THE DRAWINGS

FIGS. 10a, 10b, and 10c, are illustrations of deployment of the benthic flux sampling device and FIGS. 10d, 10e, 10f and 10g are illustrations of retrieval of the device.

DESCRIPTION OF THE PREFERRED EMBODIMENT

Figure 1:
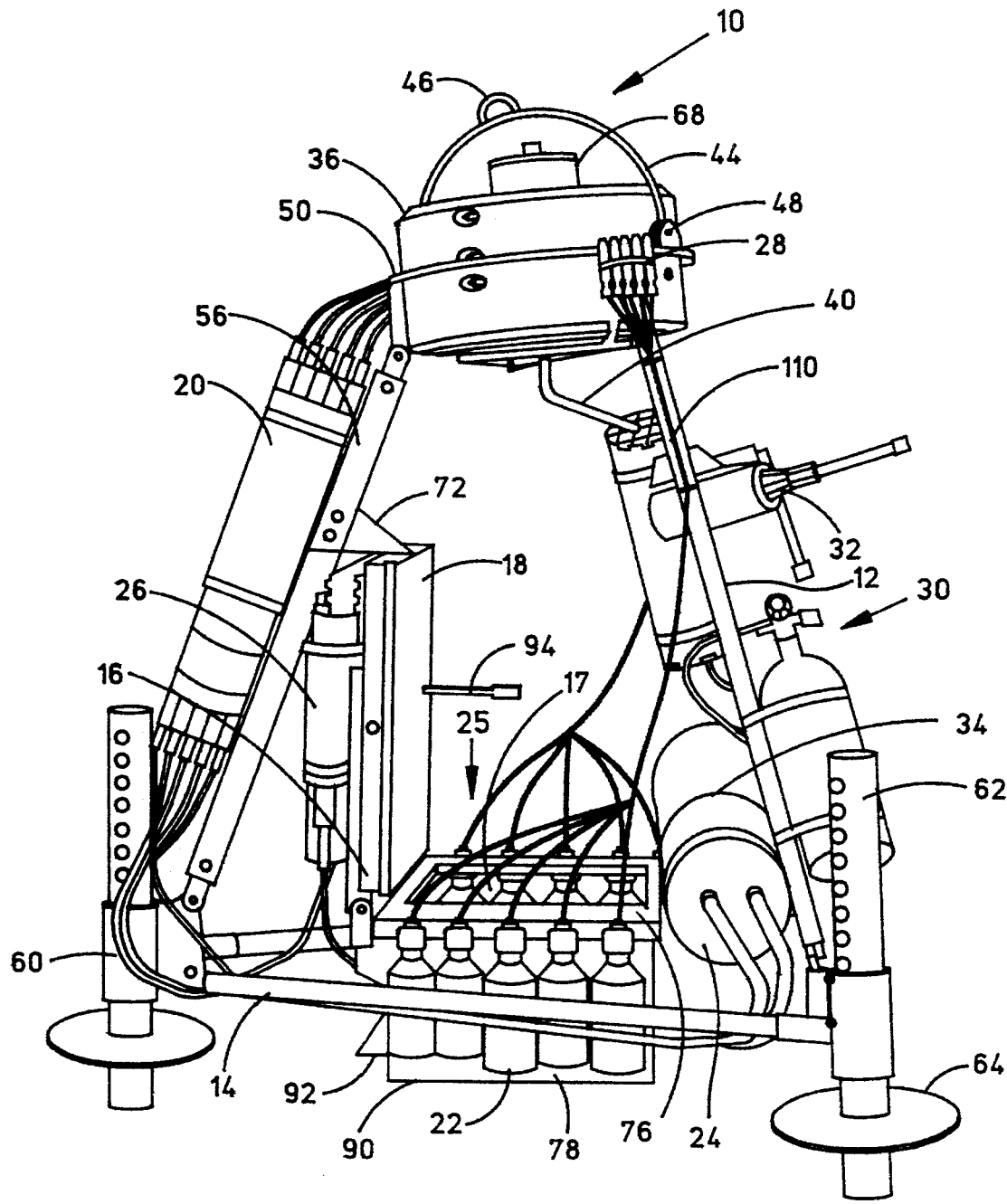
FIG. 1 is an isometric view of the benthic flux sampling device.

Referring to FIG. 1 of the drawings, an exemplary embodiment of a benthic flux sampling device 10 is shown that is capable of periodically sampling water to determine the movement of various selected toxins across a fluid boundary (e.g. ocean floor). Benthic flux sampling device 10 includes a tripod shaped frame 12 having a triangular base 14 to provided stability and to support device 10 during deployment on under water terrain. A box shaped container 16 which defines a sample chamber 17 is attached to base 14 and serves to isolate a volume of water during operation.

Several systems are included with the benthic flux sampling device to facilitate benthic flux sampling and data gathering. A fluid sampling system 25 is provided to sample water isolated within chamber 17 and store a plurality of samples. A flow-through sensor system 26 monitors conditions such as temperature, salinity, pH, dissolved oxygen content and fluid flow of water within chamber 17. These conditions effect various detectable toxin levels and are thus closely monitored to assure integrity of the sampling process in a manner to be described in greater detail below. An oxygenation system 30 is provided and is capable of replenishing oxygen lost from the water in the sample chamber due to, for example, processes which naturally occur at the ocean bottom. Accordingly, a constant amount of oxygen is maintained within a sample at ambient concentrations. Sensor system 26, sampling system 25 and oxygenation system 30 are monitored by and may be controlled by control unit 20.

Figure 2:
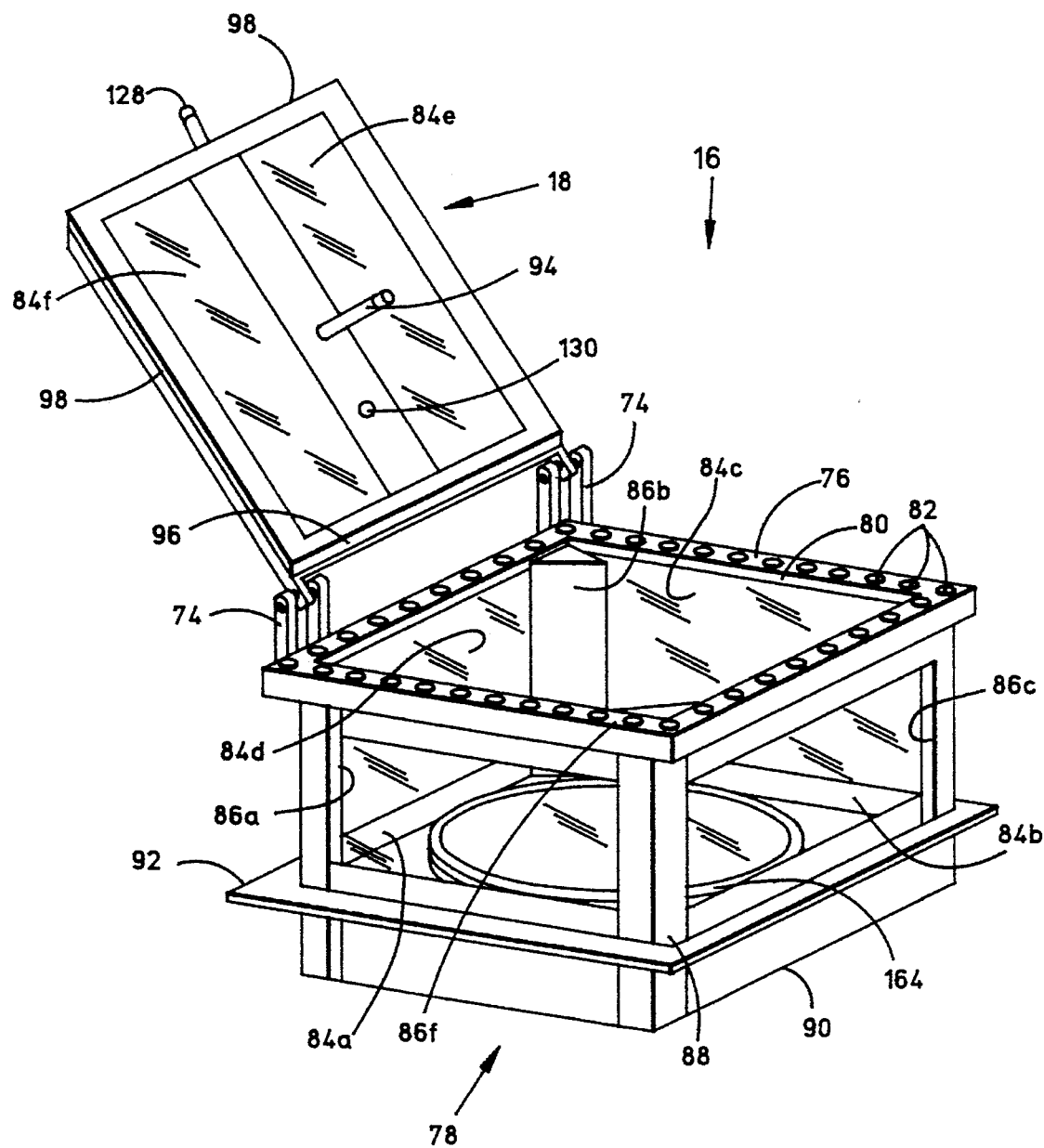
FIG. 2 is an isometric view of the container which encloses the sampling chamber of the benthic flux sampling device.
Figure 3:
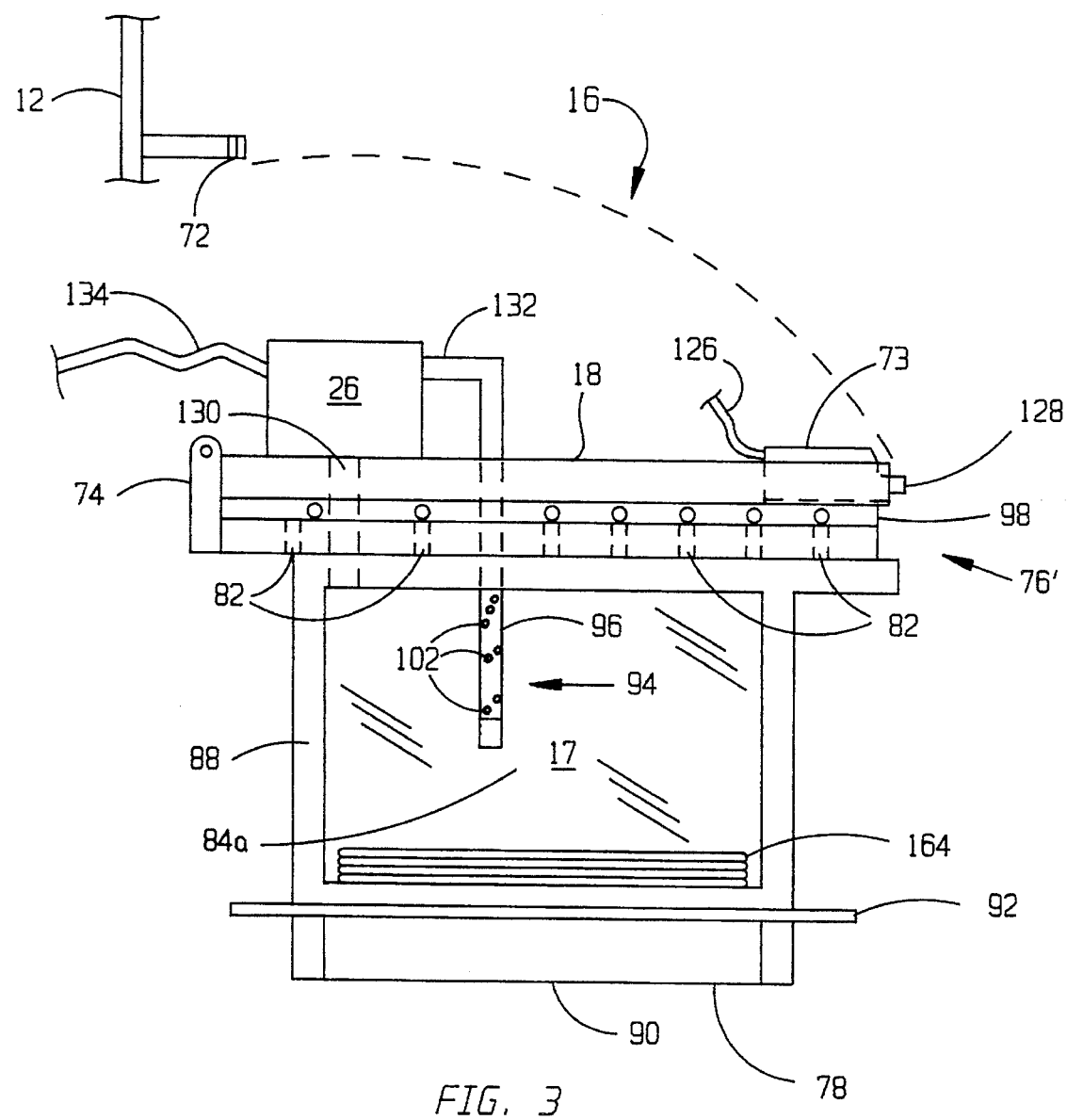
FIG. 3 is a side view of the container depicted in FIG. 2.

The preferred embodiment of container 16 of benthic flux sampling device 10 is shown in FIG. 2 and FIG. 3 and includes a frame member 76' having a top surface 76, a lid 18, an open bottom 78 and four translucent or transparent panels 84a–84d.

Lid 18 has a steel bar 98 bolted to its perimeter and is securely attached to frame member 76' of container 16 by a pair of hinges 74. Lid 18 is rotatable about hinges 74 from an open position as shown in FIG. 2 to a closed position as shown in FIG. 3 for purposes which will be elaborated on below. Lid 18 is formed with translucent panels 84e and 84f to allow ambient light to penetrate to the interior of container 16.

A multitude of bar magnets 82 are held within the perimeter of top surface 76 to hold lid 18 securely when lid 18 is closed against top surface 76. Lid 18 is slightly smaller in area than top surface 76 to align steel bar 98 with magnets 82 and to magnetically secure lid 18 in the closed position. To inhibit corrosion, a clear layer of plastic coats top surface 76 and magnets 82. A deformable tubular gasket 80 is held within the perimeter of top surface 76 inside of magnets 82 to optimize the seal between lid 18 and top surface 76. Gasket 80 may be made of silicone or any other suitable material capable of forming a water tight seal.

A lid release 73 is securely mounted to the exterior of lid 18 on a side opposing lid hinges 74. Lid release 73 includes a reciprocally moveable release bar 128 which normally protrudes beyond the periphery of lid 18. It can be appreciated by viewing FIG. 3 that when lid 18 is open, release bar 128 will engage a recessed portion of lid release hook 72 to hold lid 18 in an open position as shown in FIG. 1. Lid release 73 is also connected to lid control line 126 which is, in turn, electronically connected to control unit 20 (see FIG. 3). Accordingly, in response to an electronic signal from control unit 20, release bar 128 will be withdrawn and, due to the force of gravity, lid 18 will fall into a closed position as shown in FIG. 3.

Although lid 18 is described as a magnetically sealable hinged lid, any of a number of suitable lid types, gaskets and control mechanisms may be effectively utilized in accordance with the inventive concepts disclosed herein. One skilled in the art to which this invention pertains could therefore select other suitable lids which are able to automatically close and seal after deployment.

Bottom 78 of container 16 is provided with a knife edge periphery 90 for piercing the ocean floor during deployment to embed bottom 78 within the ocean floor and for sealing container 16 against the ocean floor. A skirt 92 surrounds the perimeter and extends horizontally outwardly from container bottom 78. More specifically skirt 92 is positioned inches above the knife edge periphery 90 of container bottom 78 to create a horizontal seal between skirt 92 and the ocean floor surface and to support container 16 when knife edge periphery is embedded in the ocean floor.

Container 16 includes a rigid support frame 88 to support transparent panels 84a–84d. Prism shaped blocks 86a–86d of transparent material are disposed in the corners of container 16 to inhibit stagnation of water in chamber 17. In the right angles formed between top surface 76 and lid 18 or between bottom 78 and the water body floor, additional blocks may be attached if desired. Blocks 86 and panels 84 are fabricated from clear polycarbonate or other high strength and non-contaminating translucent material to allow light to pass, and to minimize self-contamination and absorption.

It can be appreciated that although container 16 is box shaped and blocks 86 are referred to as prism shaped to appropriately fit into container 16, a suitable alternative configuration could be selected in accordance with this inventive concept by one skilled in the art to which this invention pertains. For example, an embodiment of benthic flux sampling device 10 may be utilized having a container which is not box shaped and where blocks 86 may be eliminated or adapted in shape and position to similarly prevent stagnation of fluid in the container and achieve the goal of benthic flux sampling.

Figure 4A:
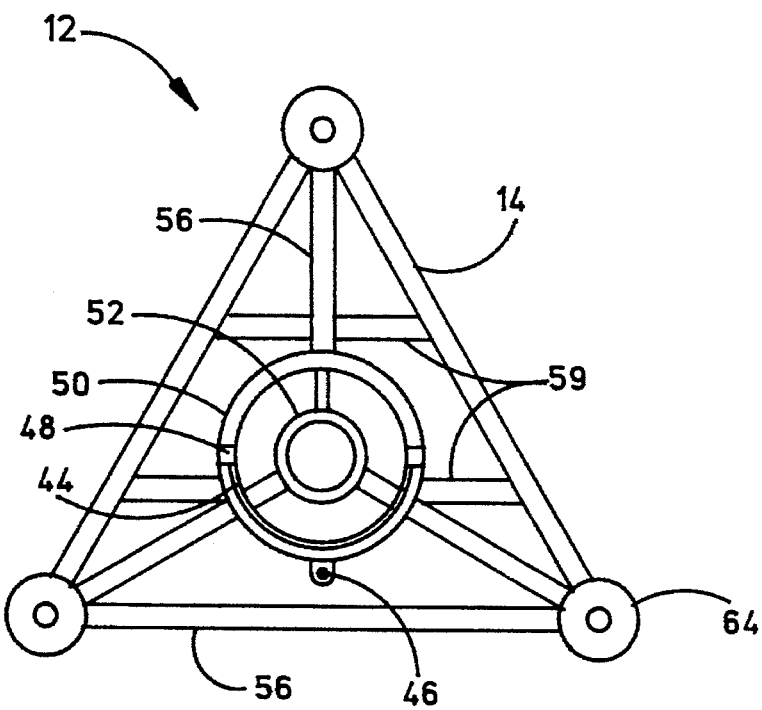
FIG. 4a and FIG. 4b are top and side views respectively of the frame of the benthic flux sampling device.
Figure 4B:
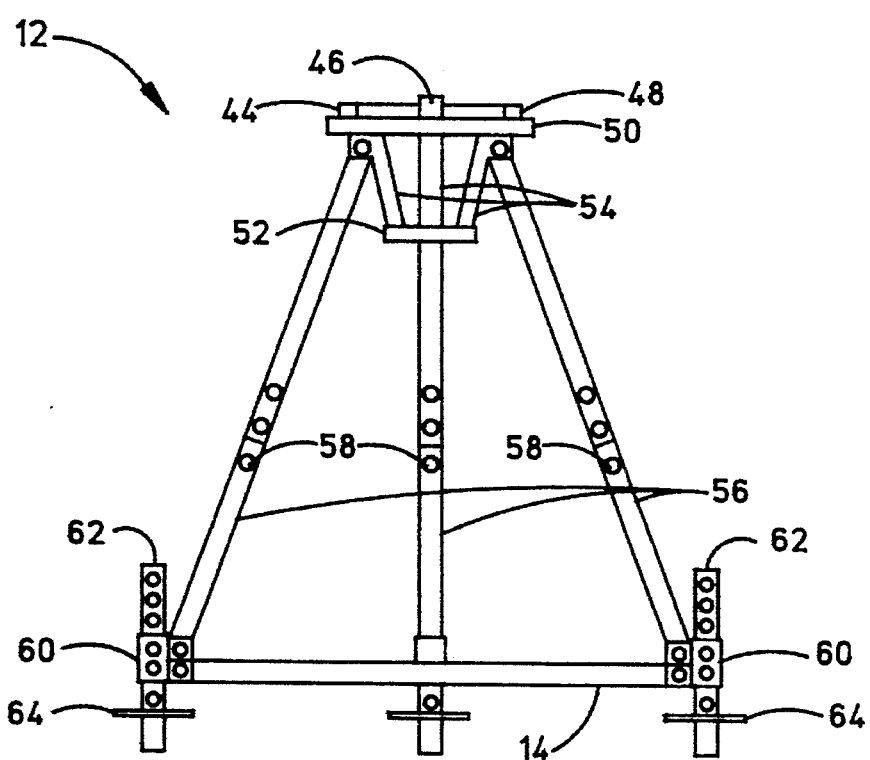

As shown in FIG. 4a and FIG. 4b, frame 12 is fabricated from a corrosion resistant material such as stainless steel or coated with an appropriate non-corrosive coating such as paint to inhibit corrosion. The weight of frame 12 combined the weight of container 16 is sufficient so that the benthic flux sampling device is non-buoyant in sea water to facilitate deployment. Additional weights may be attached to feet 64 to assure proper burial and balance during the deployment.

Frame 12 is provided with a tubular support ring 50. Ring 50 supports a lifting bail 44 having a padeye 46 to serve as a convenient grip during deployment and retrieval. Lifting bail 44 is a rigid arc shaped member having each of its two ends mounted on a respective bail hinge 48. Bail hinges 48 are, in turn, mounted on diametrically opposing points on buoy support ring 50. FIG. 1 depicts lifting bail 44 in an operational position where bail 44 extends vertically upright to allow device 10 to be hoisted upwards. FIG. 4b, alternatively, depicts lifting bail 44 in a resting position that normally lies horizontally upon support ring 50 and does not interfere with the release of retrieval buoy 36. A relatively smaller and coaxially aligned tubular buoy support ring base 52 is held by three rigidly attached buoy support arms under support ring 50 for holding buoy 36 during operation. As shown in FIG. 4b, three equal length frame arms 56 are bolted to support ring 50. The frame arms extend downward and outward from support ring 50, past ring base 52 to each of three corners of triangular base 14 to provide a rugged structure. Frame arms 56 are securely bolted to each of three mounts 60 which form the three corners of base 14. Each of the frame arms 56 are provided with a sliding frame arm adjustment 58 located near the midpoint of each to allow for a slidable adjustment so that frame is adaptable for use with various types of sensors and systems. In FIG. 4a, a pair of parallel cross bars 59 are shown attached to and extending between adjacent sides of triangular base 14 for additional rigidity and to support container 16.

Referring again to FIG. 4b, each of three cylindrically shaped legs 62 are adjustable and extend through each mount 60 for absorbing impact when the benthic flux sampling device is deployed on the ocean floor. Each leg 62 is formed with a plurality of juxtaposed holes that may be selectively vertically displaced to align with at least one hole provided in each mount 60. When each leg 62 is appropriately adjusted to a desired position so that a hole on leg 22 is aligned with a hole on mount 60, a bolt is inserted through the aligned holes to hold leg 62 in a desired extension through mount 60.

A flat disk shaped foot 64 is attached to each leg 62 at a desired position. It can be appreciated that the selective adjustment of each leg 62 can be used to optimize the sealing engagement between between container 16 and the ocean floor during deployment.

Although the preferred embodiment of frame 12 is disclosed as above, any one of a number of frame configurations could be utilized in accordance with the present inventive concept. Such configurations include any structures which support the other components on the water body floor. One skilled in the art to which this invention pertains, for example, could select any number of suitable frames to effectively accomplish the task of benthic flux sampling as substitute to the preferred embodiment disclosed above.

Referring once again to FIG. 1, a video camera 32 is attached to frame 12 on a frame arm 56 in a manner suitable to film the sealing arrangement made between container 16 and the sedimentary floor during deployment. Camera 32 may also be used during deployment of benthic flux sampling device 10 to facilitate selection of a desirable landing site. It can also be appreciated that camera 32 is useful for monitoring the sampling process and is capable of transmitting images to a remote monitor. Video camera 32 is also capable of receiving remotely transmitted instructions so that the position of camera 32 may be selected as desired and camera 32 may be selectively turned on and off.

Benthic flux sampling device 10 as shown in FIG. 1 is further provided with a two piece syntactic foam float retrieval buoy 36 that floats free from frame 12 to the water body surface in response to an acoustic signal to facilitate retrieval of benthic flux sampling device 10. A retrieval line 40 is attached between frame 12 and retrieval buoy 36 and is normally coiled in a retrieval canister 42 which is attached to frame 12 under buoy 36. After retrieval buoy 36 releases from frame 12, buoy 36 floats to the water surface, drawing retrieval line 40 from retrieval line canister 42. Buoy 36 and retrieval line 40 are retrieved at the water surface by an operator and retrieval line 40 is used to hoist the benthic flux sampling device to the water surface as shown in FIG. 10e and FIG. 10f.

Figure 5A:
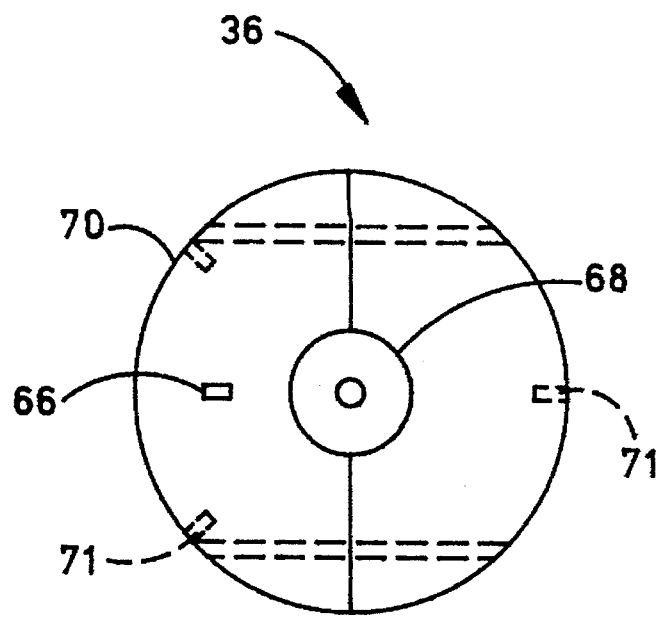
FIG. 5a and FIG. 5b are top and side views respectively of the retrieval buoy.
Figure 5B:
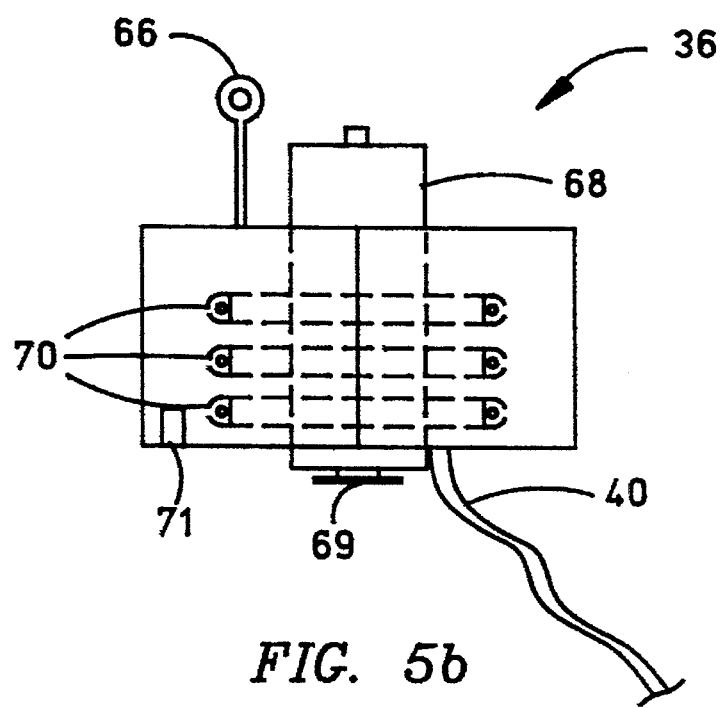

As shown in FIGS. 5a and 5b, retrieval buoy 36 is approximately cylindrically shaped and is sized to fit within buoy support ring 50 until the buoy is released. Buoy 36 is also equipped with a retrieval hook 66 to aid in retrieval. It can be appreciated by those skilled in the art that buoy 36 may be of any shape suitable to be held on frame 12 and released to the water surface to facilitate retrieval of benthic flux sampling device 10. A remotely actuated acoustic release 68 is coaxially disposed within buoy 36. The release may be actuated remotely to rotate a hook 69 which is attached to the bottom portion of acoustic release 68. Hook 69 is normally latched to frame 12 on a portion of buoy support ring base during deployment, but hook 69 unlatches from frame 12 in response to rotation caused by acoustic release 68. When released, buoyant forces lift buoy 36 from buoy support ring 50 to the water surface. Acoustic release 68 is an appropriate release such as the Endeco Type 900 Acoustic Release marketed by Endeco Corporation. This release is pre-programmable for actuation in response to a remotely initiated coded signal that increases security and prevents vandalism.

Although the preferred embodiment of the acoustically releasable retrieval buoy is disclosed as above, any one of a number of suitable retrieval system configurations could be utilized in accordance with the present inventive concept. One skilled in the art to which this invention pertains could select any number of suitable retrieval mechanisms to effectively accomplish the task of retrieving device 10 as a substitute to the preferred embodiment disclosed above.

Figure 6:
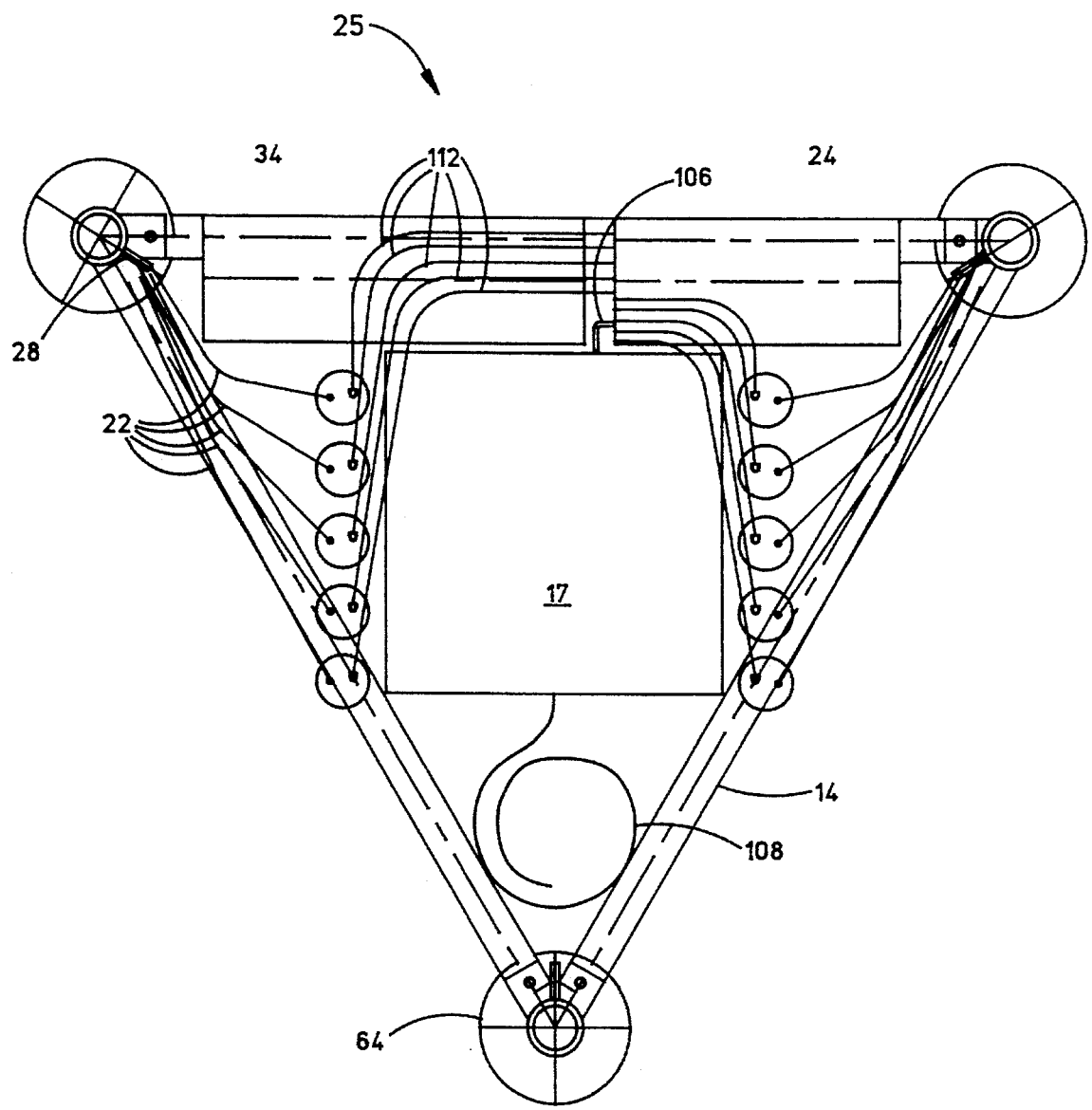
FIG. 6 is a modified top view illustrating the layout of the sampling system of the benthic flux sampling device.
Figure 7:
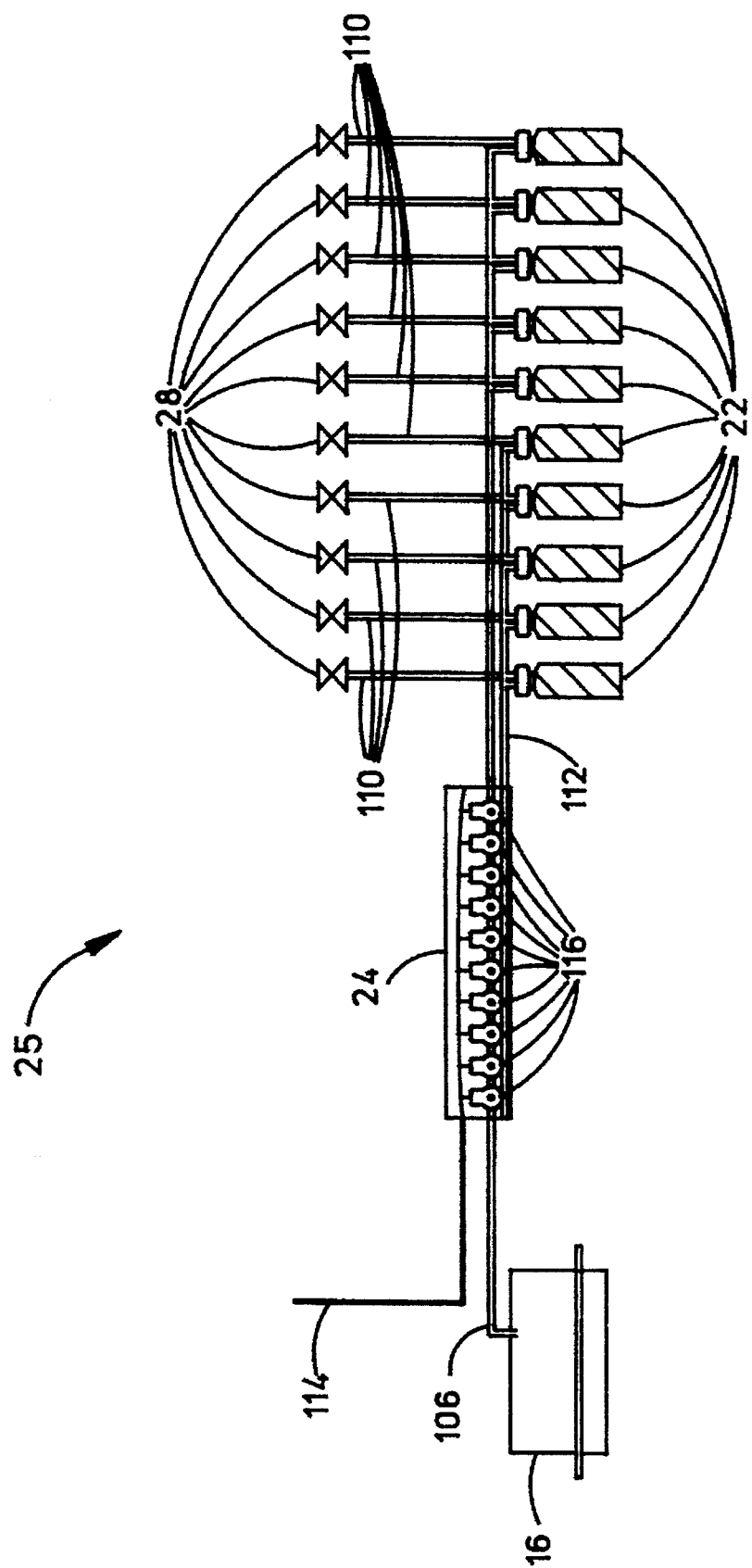
FIG. 7 is a schematic diagram of the sampling system of the benthic flux sampling device.

Looking to FIG. 6 and FIG. 7, fluid sampling system 25 is shown and includes appropriately connected supply line 106, valve manifold 24, sample lines 112, sample bottles 22, vent lines 110 and check valves 28. In the preferred embodiment of the benthic flux sampling device, sampling system 25 includes ten sample bottles 22 for periodically storing 10 separate samples from the volume of water contained in the container 16 to validate benthic flux determinations. Bottles 22 are attached, for easy removal, to base 14 in a position adjacent container 16. Each sample bottle 22 is connected in fluid communication with a corresponding valve 116 by a sampling line 112.

Valves 116 are held in a water-tight valve manifold 24 to allow valves 116 to be unaffected by deep ocean conditions during operation. Valves 116 are, in turn, connected in fluid communication with chamber 17 of container 16 through supply line 106. Valves 116 are appropriate valves such as marketed by Galtek Incorporated under the designation Galtek 203-1414-115 ¼ inch solenoid valves. Each valve is independently electronically controlled by control unit 20 through a corresponding valve control line 114.

Sample bottles 22 may be a standard design in any appropriate volume, material or shape so that bottles are easily connected and removed from with sample line 112 and vent line 110. It is intended, however, that the total volume of samples taken from chamber 17 not exceed 10% of the volume of container 16 to assure reliability of the sampling process. Bottles 22 must be strong enough to withstand underwater pressure and maintain a water tight seal. Sample bottles 22 are preferably fabricated from teflon, glass or polycarbonate depending in the toxin being measured to minimize contamination of samples and to facilitate cleaning. It can be further appreciated that sample bottles 22 may be pre-loaded with preservatives such as acid so that samples will be immediately stabilized at the moment of collection.

Check valves 28 are attached on the upper portion of frame arms 56 as depicted in FIG. 1. Check valves 28 are each connected in fluid communication with a separate sample bottle 22 through a corresponding vent line 110.

As shown in FIG. 6, replenishment line 108 is connected in fluid communication with chamber 17 and extends outwardly from the chamber to adjacent the exterior of container 16. Thus, a discrete volume of water equal to the volume of water sampled is drawn from adjacent container 16 through replenishment line 108 to instantaneously replace the volume of water taken for sampling. Sample lines 112, supply line 106, vent lines 110 and replenishment line 108 are preferably fabricated from teflon to minimize the potential for contamination of samples. Each line is attachable by means well known in the art to facilitate removal for cleaning.

Although the preferred embodiment of sampling system 25 is disclosed as above, any one of a number of suitable sampling system configurations could be utilized in accordance with the present inventive concept. Such configurations include any arrangements that sample and store fluid samples. One skilled in the art to which this invention pertains could select any number of suitable sampling systems to effectively accomplish the task of drawing and storing samples from a sampling chamber as a substitute to the preferred embodiment disclosed above.

Figure 8:
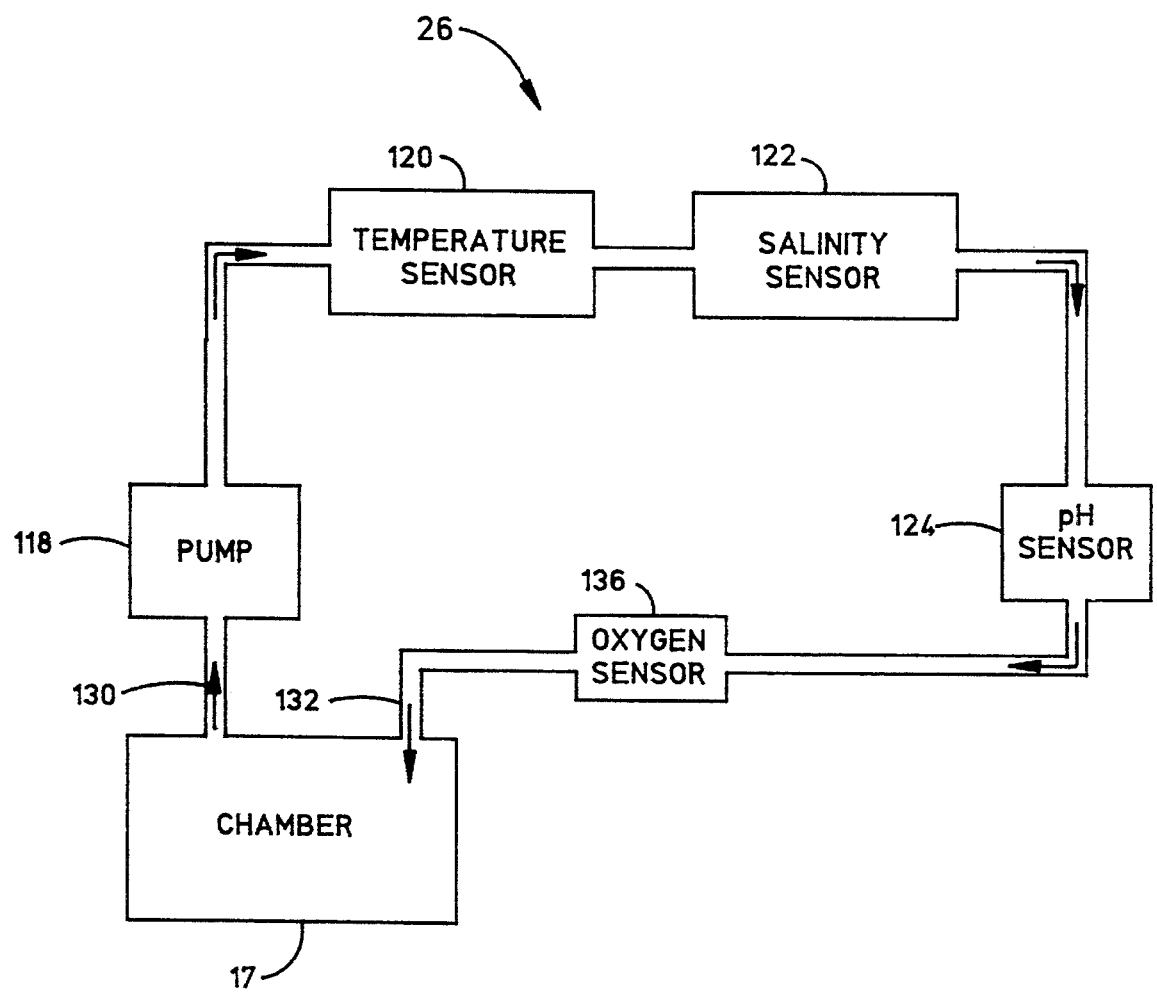
FIG. 8 is a block diagram of the flow-through sensor system of the benthic flux sampling device.

In FIG. 8, a block diagram of flow-through sensor system 26 is shown. System 26 is mounted on lid 18 and includes sensor system inlet 130 which is an opening in lid 18 to chamber 17 and a sensor system outlet 132 which is also an opening in lid 18 (see FIG. 3). Pump 118, temperature sensor 120, salinity sensor 122, pH sensor 124 and dissolved oxygen sensor 136 are mounted on lid 18 in series between inlet 130 and outlet 132 so that a fluid circuit is established to measure the required characteristics of the sample. Pump 118 maintains water circulation through the flow-through sensor system. Typically, the pump can be a commercially available submersible pump having a flow rate of approximately 90 milliliters/second; however, all pump ports which contact the volume of water in container 16 should be made of non-contaminating materials such as polycarbonate or teflon.

Temperature sensor 120 should be an aged thermistor that is pressure protected, shock and vibration resistant. Preferably an appropriate temperature sensor such as marketed by Sea Bird Electronics Corporation under the designation Model SBE 3 is used. Conductivity sensor 122 is 2-terminal, 3-electrode (platinum) flow-through type sensing element. An appropriate salinity sensor capable of use in determining salinity of ocean water is marketed by Sea Bird Electronics Corporation under the designation Model SBE 4 Conductivity Meter.

The pH sensor 124 measures the pH with a combination type probe using a pressure balanced teflon junction Ag/AgCl reference electrode. Preferably, pH sensor 124 is an appropriate sensor such as marketed by Sea Bird Electronics corporation under the designation Model SBE 18 pH sensor. The dissolved oxygen sensor 130 is preferably a "Beckman" polarographic type which produces an oxygen dependent electrical current such as that marketed by Seabird Electronics corporation under the designation Model SBE 13.

Sensors, 120, 122, 124, 136 and pump 118 are each appropriately coupled in electronic communication with control unit 20 through a sensor cable 134. Each sensor, control unit 20 and pump 118 may be suitably connected to battery case 34 to fulfill electric power be requirements. A Seabird Electronics model SBE 19 Seacat Profiler modified to facilitate control of the operation of device 10 was selected and modified to function as control unit 20 although any one of several suitable units could have been selected.

A data logger in control unit 20 periodically collects and records data such as the flow rate of pump 118, and data from each sensor within flow-through sensor system 26. Control unit 20 is electronically connected to sensor system 26 though a sensor lines 134. Control unit 20 is able to control lid closure, fluid flow by selective activation of pump 118, sensor system 26, sampling system 25 and oxygenation system 30. Control unit 20 also regulates and monitors valves 116, which are appropriately powered by batteries held in battery case 34 so that the device 10 may function autonomously.

Figure 9:
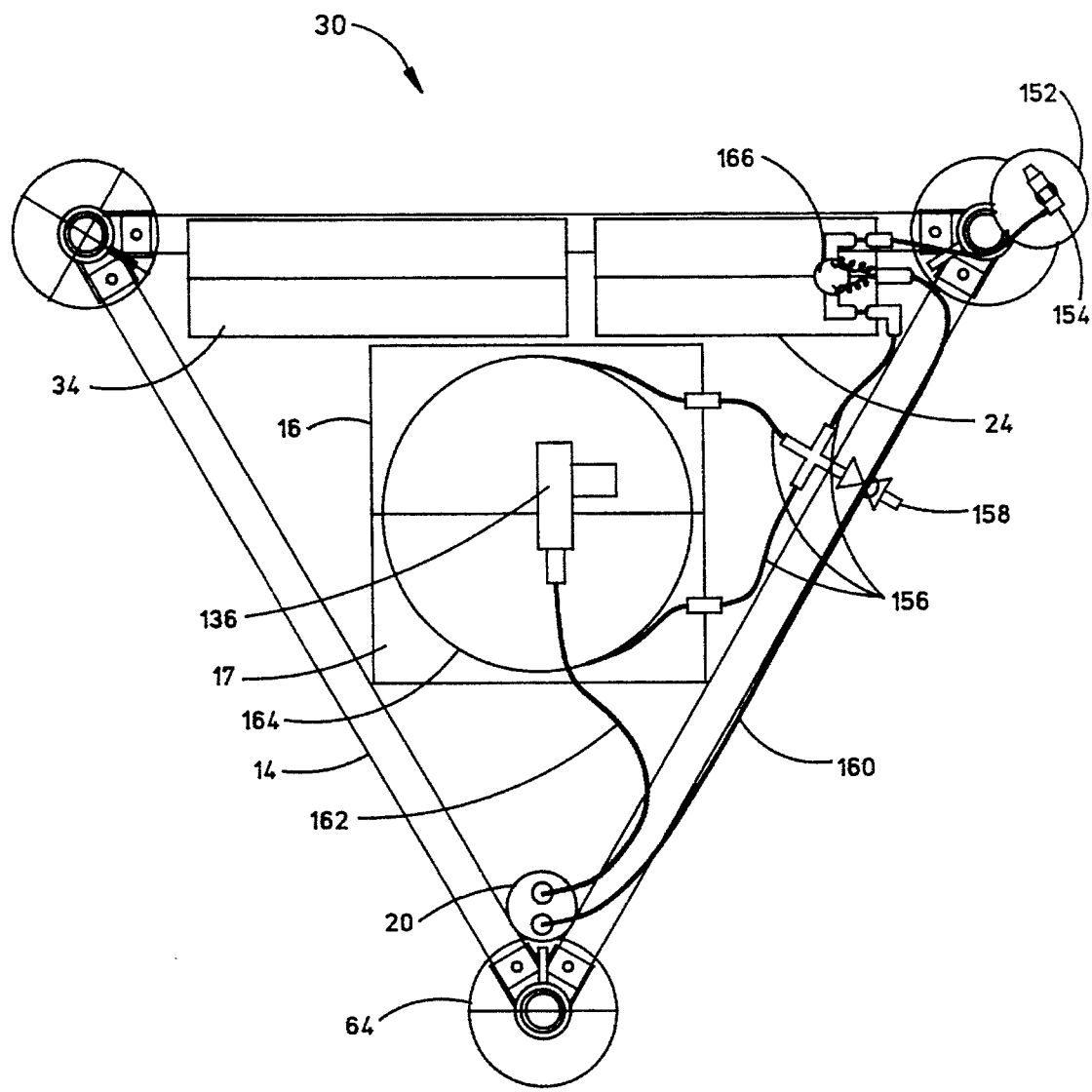
FIG. 9 is a modified top view illustrating the oxygenation system of the benthic flux sampling device.

Looking now at FIG. 9, oxygenation system 30 includes an oxygen supply tank 152, oxygen pressure regulator 154, oxygen control valve 166, diffusion coil 164 and oxygen sensor 136 for maintaining an ambient oxygenation level in the volume of water held in container 16 to facilitate a benthic flux determination. The supply tank 152 is a 13 cubic foot aluminum diving tank equipped with a first stage pressure regulator 154 for providing a suitable output pressure to the oxygenation system. Control valve 166 is a 12 volt, latching solenoid valve housed within valve manifold 24. Control valve 166 is connected by a valve control cable with control unit 20 which is, in turn, connected by a sensor cable 162 with oxygen sensor 136.

Control unit 20 utilizes feedback from the oxygen sensor 136 through oxygen sensor cable 162 to regulate control valve 166 and thereby control the flow of oxygen from supply tank 152 to chamber 17 in container 16. With this arrangement, as the dissolved oxygen concentration within the sample in container 16 dips below initial levels, oxygen sensor 136 will detect the change. This data will then be communicated to control unit 20 which will respond by opening control valve 166 to allow oxygen to pass into the chamber through diffusion coil 164. When the oxygen concentration reaches a predetermined level, (e.g. ambient level) the control valve will similarly be closed. Thus, a desired constant level of oxygen is maintained in the water sample enclosed in container 16.

Diffusion coil 164 is a thin-walled, oxygen permeable, four millimeter teflon tube having an overall length of fifty meters. The diffusion coil 164 as shown in FIG. 2 and FIG. 3 is coiled and mounted within chamber 17 in container 16. Noting FIG. 9, coil 164 is shown connected to the control valve 166 by an oxygen supply line 156 provided with an oxygen bleed valve 158 to facilitate flushing of the oxygenation system and to prevent over pressurization of oxygenation system 30.

OPERATION

Benthic flux sampling device 10 might be prepared prior to deployment to insure the integrity of the samples to be taken with the device. The entire system including the flow-through sensor system, all plumbing lines, and sample bottles may be cleaned with solutions appropriate for the analyses to be performed on the collected samples. Batteries may be charged, and a check of the acoustic release and oxygen systems may be performed to insure successful deployment, sampling and retrieval.

Benthic flux sampling device 10 can be lowered into the water following a general procedure as seen in FIGS. 10a through 10c. To lower device 10, deployment cable 168 is connected to the padeye 46 of lifting bail 44. Device 10 is deployed or placed having lid 18 open as shown in FIG. 1 to minimize disturbance of sediment during initial contact with a water body floor (e.g. ocean floor) as occurs in FIG. 10c.

Video camera 32, see FIG. 1, transmits images of the ocean floor below to an operator who locates an appropriate landing site while lowering the benthic flux sampling device as shown in FIG. 3b. When the water body floor is visible, and the surface is considered to be adequate for landing device 10, the operator raises the benthic flux sampling device from between two to four meters above the water body floor. Benthic flux sampling device 10 is then released and free falls to the ocean floor under its own weight.

The weight of the device 10 and its downward momentum will cause the knife edge periphery 90 of container 16 to pierce the sedimentary surface of the ocean floor. Thus, a seal between periphery 90 and the ocean floor is formed when benthic flux sampling device is positioned on the ocean floor as depicted in FIG. 10c. It can be appreciated that skirt 92 will contact the sedimentary surface of the ocean floor to limit the extent that periphery 90 pierces the ocean floor and to support device 10. Feet 64 of frame 12 also contact the ocean floor and function to support benthic flux sampling device 10 and container 16 an appropriate distance above the ocean floor without unduly disturbing sediment on the ocean floor during deployment. In this way, the sealing arrangement between container 16 and the water body floor is optimized and sedimentary disturbance is minimized.

After successful landing as shown in FIG. 10c, sampling procedures are initiated. The initial functions such as the closure of lid 18 and the initiation of operation of flow-through sensor system 26 are controlled by control unit 20 and may be monitored by video camera 32.

According to the preferred sequence, a signal is initiated from control unit 20 and is transmitted along lid control line 126 to lid release 73. This signal causes release bar 128 to retract and disconnect from the recess in lid release hook 71. It can be appreciated by viewing FIGS. 1 and 3 that when lid release hook 71 is retracted and no longer holds lid 18 open lid 18 will pivot about lid hinges 74 into a closed position as it is pulled downward by gravity. Once it is verified by camera 32 that the lid is closed and the procedure is proceeding correctly, cables connecting controller 20 and camera 32 may be disconnected, unplugged at the surface end, and dropped to the seafloor for a later retrieval with the rest of the benthic flux sampling device. The remainder of the procedure may be carried out autonomasly.

In this closed position, flow-through sensor system 26 is activated by control unit 20 which also engages pump 118 to draw fluid from container 16 through sensor system inlet 130 as shown in FIG. 2. As fluid flows though sensor system 26, data is sensed periodically by the various sensors. As shown in FIG. 8 the sensors may include those adapted for the determination of fluid, temperature, dissolved oxygen content, pH and salinity for example. Data is then transmitted through sensor cable 134 to control unit 20 where the data is recorded. The fluid will then be returned to container 16 through sensor system outlet 132 and helical diffuser 94 to simulate fluid flow under natural conditions and preserve the integrity of the sampling process.

The sampling process may start in response to a predetermined signal from control unit 20 through valve control line 114 to an individual sample valve 116. An individual sample valve 116 opens to allow a volume of fluid to pass from container 16 through supply line 106, past valve 116, through sample line 112 and into a sample bottle 22. Bottle 22 is vented through vent line 110 and check valve 28. It can be appreciated that fluid is caused to be drawn from container 16 into a particular bottle 22 by the hydrostatic pressure difference between check valves 28 which mounted on the upper portion of frame arms 56 and base 14 where container 16 and sample bottles 22 are mounted.

The above described sampling process maybe repeated ten times so that ten samples are obtained over a predetermined period in accordance with a pre-determined sampling routine to validate a determination of the benthic flux measurements of substances of interest. Other sampling repetitions to gather other numbers of samples may be selected as desired for a desired determination without departing from the scope of this inventive concept. From the series of samples, the benthic flux rate of toxins may be determined later in a laboratory. Throughout the sampling interval oxygenation of the volume should be maintained at an ambient level by the oxygenation system to assure valid benthic flux rate determinations.

Retrieval of the benthic flux sampling device is shown in FIGS. 10d through 10g. A hydrophone is lowered into the water and emits an acoustic signal, see FIG. 10d. In response, acoustic release 68 causes buoy to be released from frame 12 and buoy 36 floats to the ocean surface, see FIG. 10e. Retrieval hook 66 is grasped by an operator, buoy 36 is pulled into the boat and retrieval line 40 is hoisted toward the ocean surface, note FIG. 10f. A relatively stronger air lift line may be attached to release padeye 46 for lifting device 10 through the water-air interface and into the boat, see FIG. 10g.

The captured samples can be analyzed at a later time in a well equipped laboratory. The samples in the bottles are not disturbed and have been made as natural as practicable due to the efforts taken to maintain their integrity such as oxygenation, number of samples (10) and minimization of sedimentary disturbance, for example.

As disclosed, the invention provides a method for sampling benthic flux rates across a fluid boundary (i.e. the sediment at a water body floor). While the invention has been described with reference to a preferred embodiment thereof, as will be apparent to those skilled in the art, certain changes and modifications can be made without departing from the scope of the invention as defined by the following claims.

We claim:

1. A method of sampling benthic flux of a body of water comprising the steps of:

(a) enclosing a volume of said body of water within a container having an opening closed by a portion of floor beneath said body of water;

(b) maintaining an oxygen level in said volume of water substantially equal to the ambient level of said body of water; and (c) extracting samples of water from said volume of water.

2. A method of sampling benthic flux comprising the steps of:

isolating a volume of water adjacent a water body floor in a benthic flux sampling device having a container supported by three adjustable legs, each leg having a disk-shaped foot for appropriately positioning said container on said water body floor to enclose said volume and to minimize disturbing said water body floor, and provided with an open bottom having an edge engaging said water body floor, said step of isolating including embedding said edge of said container in said water body floor to enclose said volume of water in said container;

sampling said volume of water periodically with a water sampling system to deliver periodic samples of said volume of water from said container to sample receptacles attached in fluid communication with said container; and maintaining ambient dissolved oxygen levels in said volume of water during the periodic sampling with an oxygenation system attached in fluid communication with said volume of water in said container.

3. A method according to claim 2, in which said periodic sampling of said volume of water occurs up to ten times to deliver up to ten samples to up to ten sample bottles to assure validity of a benthic flux determination.

4. A method according to claim 3 further comprising:

initiating an acoustic signal to release a retrieval buoy and retrieval line from said benthic flux sampling device which float to the water body surface to enable retrieval of said retrieval line and to hoist said benthic flux sampling device from said water body floor to the surface.

5. A method according to claim 3 in which said the step of isolating includes closing a hinged lid of said container after embedding said edge to minimize disturbing of said water body floor.

6. A method according to claim 5 further comprising:

monitoring the temperature, conductivity, pH, and dissolved oxygen content of said volume of water in said container with a flow-through sensor system to assure the integrity of the sampling process.

7. A method according to claim 6, in which said container is provided with translucent panels and blocks to permit light to enter and to inhibit stagnation of water in said container, all elements in contact with said volume of water are fabricated from non-contaminating materials thereby assuring the integrity of the sampling process.

8. A method for sampling water to determine benthic flux comprising:

deploying a benthic flux sampling device on a water body floor, said benthic flux sampling device having:
a frame,
a container mounted on said frame, said container having an open bottom engaging said water body floor,
sample receptacles secured on said frame,
a water sampling system mounted on said frame in fluid communication with said container and said sample receptacles, and
an oxygenation system attached to said frame, said oxygenation system being in fluid communication with said container and said container, said sample receptacles and said water sampling system being fabricated from non-contaminating materials; and isolating a volume of water in said container by placing said open bottom against said water body floor;

oxygenating said volume of water at a constant oxygen level with said oxygenation system;

periodically sampling said volume of water isolated in said container with said sampling system and storing each sample in a separate one of said sample receptacles; and retrieving said benthic flux sampling device.

9. A method for sampling water to determine benthic flux comprising:

deploying a benthic flux sampling device on a water body floor, said benthic flux sampling device having:
a frame,
a container mounted on said frame, said container having an open bottom engaging said water body floor, said open bottom of said container being formed with a knife edge periphery and a skirt extending horizontally outwardly from the perimeter of said open bottom, said skirt and said knife edge periphery engaging said water body floor when contact is made between said open bottom and said water body floor,
sample receptacles secured on said frame;
a water sampling system mounted on said frame in fluid communication with said container and said sample receptacles, and
an oxygenation system secured to said frame,
said oxygenation system being in fluid communication with said container and said container, said sample receptacles and said water sampling system being fabricated from non-contaminating materials;

isolating a volume of water between said container and said water body floor by placing said open bottom against said water body floor;

maintaining a constant oxygen level within said container by selectively employing said oxygenation system to introduce oxygen into the water held in said container;

periodically sampling water isolated in said container with said sampling system and storing each sample in a separate one of said sample receptacles; and retrieving said benthic flux sampling device.

10. A method according to claim 9 in which said container is formed with an open top surface, said open top surface having a hinged lid mounted for sealing against said open top surface and isolating said volume of water within said container.

11. A method according to claim 10 in which said container has translucent panels and blocks to allow ambient light to enter said container to minimize disruption of light driven processes and to inhibit stagnation of fluid within said container.

12. A method for sampling water to determine benthic flux comprising:

deploying a benthic flux sampling device on a water body floor, said benthic flux sampling device having:
a frame,
a container mounted on said frame, said container having an open bottom engaging said water body floor,
sample receptacles secured on said frame,
a water sampling system mounted on said frame in fluid communication with said container and said sample receptacles, and
an oxygenation system secured to said frame, said oxygenation system being in fluid communication with said container and said container, said sample receptacles and said water sampling system being fabricated from non-contaminating materials; and isolating a volume of water between said container and said water body floor by placing said open bottom against said water body floor;

maintaining a constant oxygen level within said container by selectively employing said oxygenation system to introduce oxygen into the water held in said container;

periodically sampling water isolated in said container with said sampling system and storing each sample in a separate one of said sample receptacles;

retrieving said benthic flux sampling device;

drawing water from said container with a flow-through sensor system attached to said lid;

monitoring and periodically recording the temperature, pH and salinity of the water drawn from said container; and returning the drawn water to said container.

13. A method according to claim 11 further comprising:

diffusing said water upon return to said container with a tube shaped helical diffuser mounted on said lid and extending into said container, said helical diffuser having an entrance attached in fluid communication with said flow-through sensor system and a multitude of holes aligned in a helix pattern along said diffuser for allowing water to exit from said diffuser into said container to inhibit stagnation of water in said container.

14. A method for sampling water to determine toxin flux rates through benthic sediments at a water body floor comprising:

deploying a benthic flux sampling device on a water body floor, said device having;

a frame formed with a base;

a container mounted on said base, said container having an open top surface and an open bottom, said open bottom being formed with a knife-edge periphery for sealing against said water body floor;

a hinged lid mounted on said open top surface for closing against said open top surface to isolate water between said container and said water body floor;

a water sampling system in fluid communication with said container and attached to said frame, said sampling system having a plurality of sample bottles mounted on said frame and attached in fluid communication with said container for storing water; and an oxygenation system attached in fluid communication with said container for delivering oxygen to said container to maintain the dissolved oxygen content of water in said container;

isolating a volume of water between said container and said water body floor;

delivering oxygen to said volume of water with said oxygenation system;

periodically sampling said volume of water with said sampling system; and retrieving said benthic flux sampling device.

15. A method according to claim 14 in which said base is triangular shaped having three adjustable, cylindrical legs each being extendable from each corner of said base and each of said legs being formed with a disk-shaped foot to support said container and minimize disturbance of said water body floor during deployment.

16. A method according to claim 14 in which said benthic flux sampling device is provided with a retrieval buoy and a coiled retrieval line coupled to and disposed on said frame, and said retrieval buoy and a coiled retrieval line are releasable in response to a coded remote signal.

17. A method according to claim 14 further comprising:

monitoring the temperature, pH, dissolved oxygen content and salinity of water in said container with a flow-through sensor system mounted on said lid and in fluid communication with said container.

18. A method according to claim 17 further comprising:

recording data gathered by said sensor system with a control unit in electronic communication with said sensor system.

19. A method according to claim 18 in which the step of sampling includes drawing fluid from said container through a sample line into a sample bottle by opening a corresponding check valve attached in fluid communication with said sample bottle through a vent line to utilize the hydrostatic pressure difference between said check valve and said container to draw water from said volume of water in said container into said sample bottle.

20. A method according to claim 19 in which said sampling is regulated by said control unit, said control unit is in electronic communication with valves that are each attached in fluid communication between a sample line and a sample bottle, and said valves are electronically controlled by said control unit to regulate said sampling.

21. A method according to claim 14 in which a multitude of magnets are aligned within the perimeter of said top surface and a metal bar surrounds the perimeter of said lid to magnetically seal against said magnets when said top is closed.

22. A method according to claim 1 in which said step of enclosing includes the step of engaging said floor with a portion of said container to isolate said volume of water.

23. A method according to claim 22 in which said step of engaging includes the step of sealing said volume of water from ambient water by said portion on said floor.

24. A method according to claim 1 in which said step of maintaining includes the step of monitoring said oxygen level.

25. A method according to claim 23 in which said step of maintaining includes the step of monitoring said oxygen level.

26. A method according to claim 1 in which said step of maintaining includes the step of monitoring temperature, pH, dissolved oxygen content, and salinity of said volume of water.

27. A method according to claim 1 in which said step of maintaining includes the step of oxygenating said volume of water to said oxygen level.

28. A method according to claim 24 in which said step of maintaining includes the step of oxygenating said volume of water to said oxygen level.

29. A method according to claim 25 in which said step of maintaining includes the step of oxygenating said volume of water to said oxygen level.

30. A method according to claim 1 in which said step of extracting comprises the step of periodically extracting said samples of water.

31. A method according to claim 28 in which said step of extracting comprises the step of periodically extracting said samples of water.

32. A method according to claim 29 in which said step of extracting comprises the step of periodically extracting said samples of water.

33. A method according to claim 1 further comprising:

the step of storing said samples of water and the step of retrieving said samples of water.

34. A method according to claim 31 further comprising:

the step of storing said samples of water and the step of retrieving said samples of water.

35. A method according to claim 32 further comprising:

the step of storing said samples of water and the step of retrieving said samples of water.

* * * * *